US011003048B1

(12) United States Patent
Rawlani et al.

(10) Patent No.: US 11,003,048 B1
(45) Date of Patent: May 11, 2021

(54) POLARIZED IMAGING APPARATUS FOR USE WITH A MOBILE DEVICE

(71) Applicant: VG Technology Inc., Wilmington, DE (US)

(72) Inventors: Vinay Rawlani, Columbia, MO (US); Tomasz Jan Budzen, Chicago, IL (US)

(73) Assignee: VG Technology Inc., Wilmington, DE (US)

(*) Notice: Subject to any disclaimer, the term of this patent is extended or adjusted under 35 U.S.C. 154(b) by 0 days.

(21) Appl. No.: 16/713,939

(22) Filed: Dec. 13, 2019

(51) Int. Cl.
*G03B 11/00* (2021.01)
*G03B 15/05* (2021.01)
*A61B 17/00* (2006.01)

(52) U.S. Cl.
CPC .............. *G03B 11/00* (2013.01); *G03B 15/05* (2013.01); *A61B 2017/00747* (2013.01); *G03B 2215/0517* (2013.01); *G03B 2215/0592* (2013.01)

(58) Field of Classification Search
CPC ...... G03B 2215/0592; G03B 2215/056; G03B 15/14; G03B 17/56; G03B 17/565; G03B 17/566; G03B 11/00; A61B 2017/00747; A61B 5/0077
See application file for complete search history.

(56) References Cited

U.S. PATENT DOCUMENTS

| | | | | |
|---|---|---|---|---|
| 7,376,346 B2* | 5/2008 | Merola | ................. | A61B 5/0071 348/77 |
| 8,774,619 B2* | 7/2014 | Harris | ................... | G02B 27/28 396/544 |
| 2006/0251408 A1* | 11/2006 | Konno | ................... | G01J 3/0291 396/14 |
| 2014/0313377 A1* | 10/2014 | Hampton | ............... | A45C 11/00 348/241 |
| 2015/0355527 A1* | 12/2015 | Takahashi | .......... | H04N 5/23293 348/371 |
| 2018/0140196 A1* | 5/2018 | Khosravi Simchi | ... | A61B 90/36 |
| 2018/0164672 A1* | 6/2018 | Rebot | ................... | H04R 1/028 |
| 2020/0106932 A1* | 4/2020 | Chou | ................... | H04N 5/2252 |

FOREIGN PATENT DOCUMENTS

| | | |
|---|---|---|
| CN | 103181154 A | 6/2013 |
| CN | 103959040 B | 12/2017 |
| CN | 206894769 U | 1/2018 |

(Continued)

*Primary Examiner* — Christopher E Mahoney
(74) *Attorney, Agent, or Firm* — Perkins Coie, LLP

(57) ABSTRACT

Apparatus for obtaining polarized imagery using a portable device, comprising a light source, a first polarizing filter configured to cover the light source, a second polarizing filter configured to cover the lens of a mobile device's built-in camera, one or more housing to contain the light source and filters, and couplers attached to the housings for coupling the housings to the mobile device. When the housing is coupled to the mobile device and the camera is operated, light from the light source passes through the first polarizing filter, then passes as polarized light through an illuminating path to illuminate an object being imaged. Then light from the illuminated object passes through an optical path, through the second polarizing filter to the camera lens. In embodiments, the axis of polarization of at least one of the polarizing filters can be modified to allow for cross, parallel and variable polarized imaging.

20 Claims, 12 Drawing Sheets

(56) References Cited

FOREIGN PATENT DOCUMENTS

| | | | |
|---|---|---|---|
| EP | 1860488 | A2 | 11/2007 |
| EP | 1860488 | A3 | 11/2008 |
| EP | 1860488 | B1 | 6/2016 |
| JP | 2007206137 | A | 8/2007 |
| JP | 2011069942 | A | 4/2011 |

\* cited by examiner

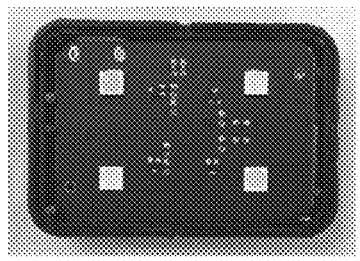 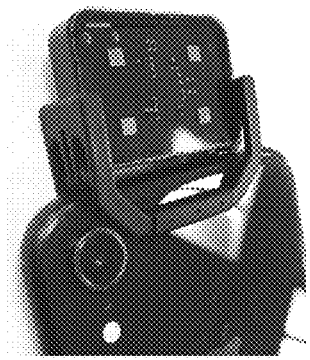 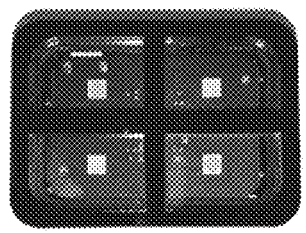
FIG. 1A  FIG. 1B  FIG. 1C
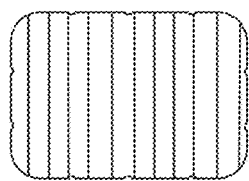 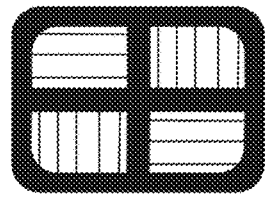 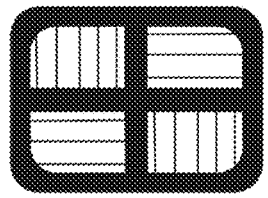
FIG. 1D  FIG. 1E  FIG. 1F

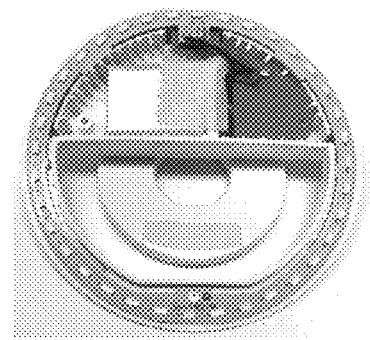
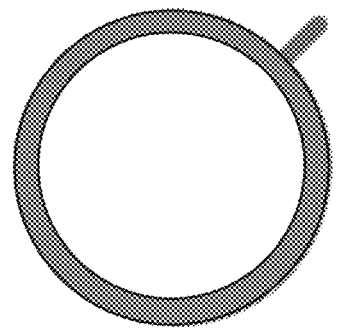
FIG. 6A　　　　FIG. 6B
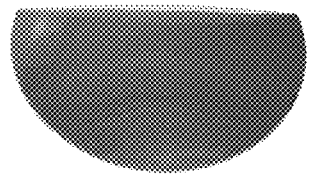
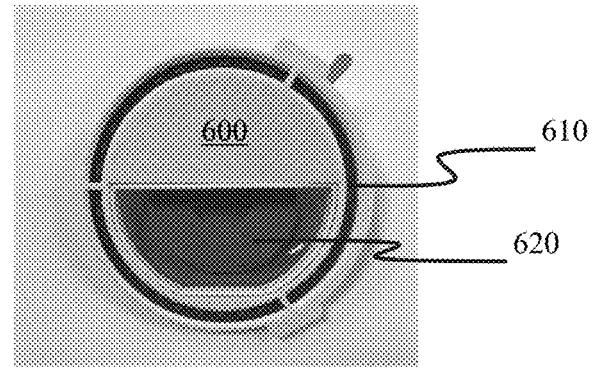
FIG 6C　　　　FIG 6D

 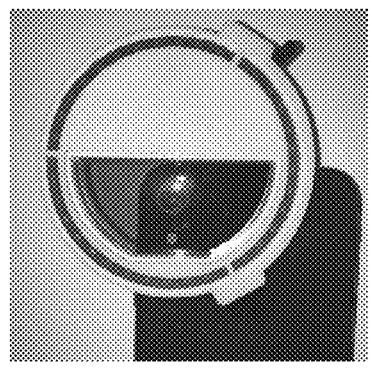 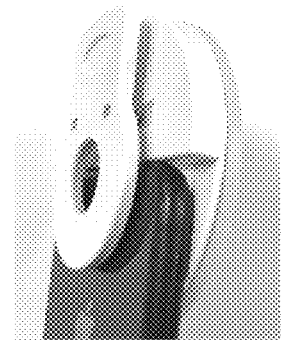
FIG 7A  FIG 7B  FIG 7C
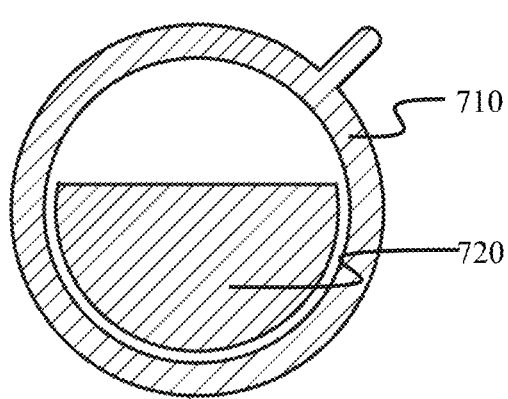 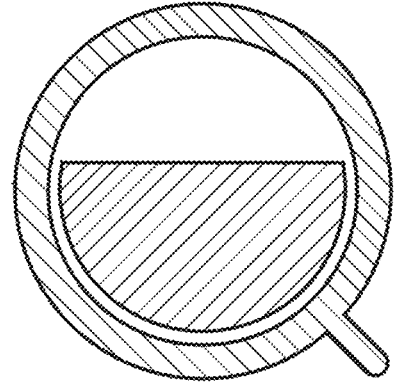
FIG 7D  FIG 7E

POLARIZED IMAGING APPARATUS FOR USE WITH A MOBILE DEVICE

BACKGROUND

Polarization allows for differential imaging of surface and subsurface layers of organic and inorganic objects. In the process of polarized imaging, a light emitted from a light source is polarized along a given axis by a filter before illuminating an object. Upon reaching the object, this polarized light may be reflected from the surface or enter the object and be absorbed, refracted, scattered and/or fluoresced. In the case in which the light is reflected from the object's surface, the light maintains the original axis of polarization. In cases in which light enters the object, the light is depolarized. When viewing the object with an optical sensor such as a camera or eye, a second polarizing filter may be placed in the optical path between the object and the optical sensor. If the axis of polarization of the second polarizer is parallel to the axis of first polarizer, light reflected from the surface of the object is passed through the second filter unobstructed and is received by the sensor. However, light with different axes of polarization such as those emitted from the subsurface which has been depolarized is blocked. This allows for clear visualization of the surface while minimizing the background noise of the subsurface. Conversely, if the axis of polarization of the second polarizer is perpendicular to the axis of the first, light reflected from the surface of the object is blocked from being received by the sensor, allowing light from the subsurface to be preferentially received by the sensor. This allows for better visualization of the subsurface, while minimizing the background noise of the surface. The second polarizer may also be placed in variable axes in relation to the first polarizer to achieve variable combinations of polarized imaging.

Cross polarization have known benefits in dermatology, dentistry, forensics, gemology, paleontology, photography and other specialties in which subsurface imaging or removal of surface glare is useful. For example, in dermatology, cross polarization is used to evaluate lesions by minimizing glare of the skin surface, allowing for more detailed analysis of subsurface structures such as vasculature or pigmentation. In dentistry, cross polarization is used to decrease glare on teeth to allow for more accurate color matching of resins.

Polarized imaging requires a polarized light source and a polarized optical receiver. There are several apparatuses in which flash/strobes are connected to digital cameras with polarizing filters placed in front of both the camera and flash. Polarized imaging devices are also available without cameras. In these cases, a polarized light source is used to illuminate an object that is viewed by an operator through a polarized window. These polarized imaging devices tend to be expensive and are not intended for mobile imaging.

Mobile devices have made imaging technology more accessible and cost-effective. However, a polarized imaging apparatus for mobile devices is not available nor have been described outside of a specific use case of dermoscopy. Dermatoscopes are commonly utilized by dermatologist to view individual skin lesions or small areas of the skin. Digital dermatoscopes are compatible with mobile devices. They function by providing polarized light that illuminates the skin combined with a second polarizer and magnifying lens in front on the mobile device's camera. However, these devices are specifically used for evaluation of small areas no larger than approximately 5 cm. Since digital dermatoscopes contain optics with short focal lengths, small field of view and magnification, they cannot be used for other imaging purposes. For example, dermatoscopes are not able to image larger areas such as multi-lesion patterns of pigmentation, inflammation, and actinic damage. Nor can dermatoscopes be used for dentistry, forensics, or the other specialties listed earlier.

Apparatuses for generalized polarized imaging on mobile devices are not available. The polarizers that are available for mobile devices are limited to the camera (receiving sensor) and not the illuminating source (LED or flash). Polarization of only the mobile device camera has limited effectiveness because the light which illuminates the objects is not polarized. Instead, polarizers for mobile cameras function to partially reduce surface glare to better visualize objects, but are not intended for detailed viewing of subsurface elements. To view the subsurface in detail controlled polarized lighting is necessary. There are several generalized external lighting devices available for mobile devices, but none that incorporate variable polarization outside of dermoscope-type devices.

Polarized imaging can also be combined with other imaging techniques. For example, cross polarization can be combined with spectral imaging in dermatology. In spectral imaging, various wavelengths of light penetrate the skin to different depths and exhibit variable absorption patterns with chromospheres in the skin such as hemoglobin and melanin. These characteristics allow use of various spectra (wavelengths) of light to target specific structures within the skin to enhance visualization. When spectral imaging is combined with cross polarization, the surface glare can be excluded allowing for even better visualization of targets.

Thus, there is a need for an apparatus that can be used with a smart phone or other mobile device equipped with a camera, which enables economical and effective polarized imaging.

SUMMARY

Apparatus for obtaining polarized imagery using a portable device, comprising a light source, a first polarizing filter configured to cover the light source, a second polarizing filter configured to cover the lens of a mobile device's built-in camera, one or more housings to contain the light source and filters, and couplers attached to the housing(s) for coupling the housing(s) to the mobile device. When all housing is coupled to the mobile device and the camera is operated, light from the light source passes through the first polarizing filter, and passes as polarized light through an illuminating path to illuminate an object being imaged, and light from the illuminated object passes through an optical path and the second polarizing filter to the camera lens. In embodiments, the axis of polarization of at least one of the polarizing filters can be modified to allow for cross, parallel and variable polarized imaging.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and aspects, and together with the description serve to explain the principles of the invention, the scope of which is determined by the claims.

In the drawings:

FIGS. 1A to 1F illustrate aspects of an exemplary embodiment comprising a housing holding LEDs and filters, that may be clipped onto a mobile device to provide multiple polarized light sources.

FIGS. 6A to 6D illustrate aspects of an exemplary embodiment of a device containing a light source, rotating first polarizing filter in front of the light source, and second polarizing filter which is positioned in front of the mobile device camera when the apparatus is coupled to the mobile device.

FIGS. 7A through 7E illustrate aspects of the embodiment of FIG. 6 coupled to a mobile device.

DETAILED DESCRIPTION

Figure 2A:
FIGS. 2A and 2B show the application of a filter embodiment to a camera of an iPhone.

It is to be understood that the figures and descriptions provided herein may have been simplified to illustrate aspects that are relevant for a clear understanding of the herein described processes, machines, manufactures, and/or compositions of matter, while eliminating, for the purpose of clarity, other aspects that may be found in typical devices, systems, and methods. Those of ordinary skill in the pertinent art may recognize that other elements may be used, or may be required to implement the devices, systems, and methods described herein. Because such elements and steps are well known in the art, and because they do not facilitate a better understanding of the present disclosure, a discussion of such elements and steps may not be provided herein. However, the present disclosure is deemed to inherently include all such elements, variations, and modifications to the described aspects that would be known to those of ordinary skill in the pertinent art.

It will be readily understood that the components of the present invention, as generally described herein and illustrated in the figures, may be designed and arranged in a variety of different configurations. Thus, the following detailed description of embodiments is not intended to limit the scope of the invention as claimed, but is merely representative of selected illustrative embodiments of the invention. The usage of the phrases "embodiments", "example embodiments", "some embodiments", or other similar language refers to the fact that a particular feature, structure, or characteristic described may be included in at least one embodiment of the present invention, and do not necessarily all refer to the same embodiment or group of embodiments. Thus, the described features, structures, or characteristics may be combined in any suitable manner in one or more embodiments.

A variety of embodiments will now be described. These are provided as teaching examples and should not be interpreted to limit the scope of the invention defined by the claims. Although specific details and aspects of certain illustrative embodiments are presented, the embodiments may be modified by changing, supplementing, or eliminating many of these details.

General

In exemplary embodiments, a first filter may be coupled to cover a light emitting source. A second filter may also be coupled to the mobile device to cover a camera's optical input. The first filter directly modifies the light emitted from the light source that illuminates an object of interest, and the second filter directly modifies light from the illuminated object received by the camera. In embodiments, both filters are polarizing filters, at least one of which may have an axis of polarization that can be modified to provide for variable-polarized imaging. The filters can be used with mobile devices such as smart phones, digital cameras, video cameras, tablets, and the like having at least one camera with a field of view illuminated by the light source. Moreover, the apparatus may, but need not, contain optical elements such as lenses, filters, diffractors or the like.

Light Source

In embodiments, at least one light emitting source is used to illuminate the object of interest. The light may be supplied by any source including but not limited to incandescent, luminescent, LED, flash element, or laser. The light emitted from the source may be any wavelength or combination of wavelengths including ultraviolet (UV), visible, and/or infrared. The light may be powered by any energy source such as battery, rechargeable battery, AC/DC corded power, or other external power source such as the mobile device. The intensity and wavelength output of the light of the light source may be controlled manually, automatically, by remote device, by software loaded within the light source itself, by software loaded on a such as the mobile device, or by response to a sensor such as an optical photodiode. There may by a multitude of illuminating elements within the light source. Each element may be independently controlled or the elements may be controlled as a group. The light source may be coupled to the mobile device or other housing by adhesion, via a fitting or clamp, or via another attachment. Coupling maybe temporary or permanent.

Camera

In embodiments, a polarizing filter is positioned in front of mobile device's camera. The camera may be a single camera or a multitude of cameras on the mobile device. If the mobile device is a mobile phone, any of its front-facing cameras or any of its rear-facing cameras may be utilized. The camera may be capable of photography or videography. The camera may have other external lenses and filters. The camera may be capable of visible, UV or IR imaging or a combination of any of the three. The camera of the mobile device may itself be natively polarized by one of the optical elements internal to the mobile device.

Polarizing Filter

In embodiments, a polarizing filter is used to polarized the light along the illuminating path between the light source and the object, as well as the optical path between the object and the camera. The polarizer may have a multitude of properties. The polarizer may be in a variety of forms including iodine-type or and dye-type. The polarizer maybe linearly, circularly, elliptically polarized. The axis of polarization can be selectively determined. In the case of circular or elliptical polarizers, the handedness may be right or left. The transmission and extinction ratings of the polarizer may be selectively determined. The polarizer may filter UV, IR and/or visible light. The polarizer may be of any particular color or combination of colors. The polarizer may be coupled, laminated or sandwiched with other materials such as but not limited to cellulose triacetate, plastic or glass. The polarizer may be hard coated with anti-reflective, anti-glare, clear, or any other hard coating. Polarizing material suitable for use in embodiments are available from multiple manufacturers. For example, websites from which polarizing materials are currently available online include https://www.apioptics.com, https://3dlens.com/linear-polarizer-film.php, https://www.edmundoptics.com/c/polarization/620/, and http://polarization.com.

In embodiments, any of the foregoing may be used in conjunction with at least one additional light modifier. The additional light modifier(s) may include, without limitation, one or more lenses, such as concave or convex, single or double, aspherical, cylindrical, or the like; prisms, mirrors, diffractors, diffusers, and/or contrast enhancing or other filters to provide image magnification, band pass, short pass, long pass, narrow band, and the like, for advanced imaging. Such imaging may include spectral, multispectral, fluorescent, or other desired modalities. Sources of such light modifiers filters may include, for example, https://us.rosco.com/en/products/family/filters-and-diffusions, and https://www.edmundoptics.com/c/optical-filters/610/.

Polarization of Light Source (First Polarizer)

In embodiments, at least one first polarizing filter is placed in front of the light source in the illuminating path between the light source and the object being illuminated. The first polarizing filter may be positioned in front of the light source in various ways. The first polarizing filter may be temporarily or permanently adhered or coupled to the light source or the housing of the light source. The first polarizing filter may be housed within another structure, which itself is temporarily or permanently adhered or held in position to the light source or the housing of the light source. The first polarizing filter and lighting may also be enclosed in the same housing. The first polarizing filter may be held still or may be free to move such that the filter can be repositioned (rotated, flipped, etc.) or exchanged to alter the axis of polarization. The axis of polarization may be changed by manually manipulating the polarizer, or a first polarizer may be moved by a motorized device, which may be manually or automatically switched (e.g., controlled by physical switches or by software settings). The housing may move the first polarizing filter into place in front of the light source. If there are multiple lighting elements in the illuminating source, a first polarizer may be positioned in front of a single element, a group of elements, or all elements. Different illuminating elements may have polarizers with varying axes of polarization or other properties. For example, when a plurality of illuminating source are present, a subset may be paired with a horizontal-axis polarizer, another subset may be paired with a vertical-axis polarizer, and another subset may be paired with a polarizer any other axis between 0 and 90 degrees.

In embodiments, the housing of the light source and/or first polarizing filter may be coupled to the mobile device. The housing may be temporarily or permanently adhered, fitted, clamped, or coupled in another manner to the mobile device.

Polarization of Camera (Second Polarizer)

In embodiments, at least one second polarizing filter is placed in front of a mobile device camera in the optical path between the object being illuminated and the camera. In embodiments, the second polarizer may be coupled to the mobile device camera in a multitude of ways, either temporarily or permanently. The second polarizer may be laminated with an adhesive such as 3M 821x optically clear adhesive and applied to the mobile device camera. The second polarizer may be housed within an apparatus that is adhered to the mobile device. In embodiments, second polarizer can be coupled with a housing, where the housing is structured to hold the polarizing filter in front of the mobile device's camera while the housing is coupled to the mobile device's camera. In other embodiments, the second polarizing filter may also be integrated in to the housing containing the light source and first polarizer such that when the housing is couple to the mobile device the second polarizing filter is position in front of the mobile device camera.

In embodiments, the second polarizer may be fixed, exchangeable, or allowed to change position. The second polarizer may change positions within the housing or the housing itself may change orientation to change its axis of polarization or position the polarizing filter in front of the camera. The axis of polarization may be manually manipulated, or a second polarizer may be moved by a motorized device, which may be manually or automatically switched (e.g., controlled by physical switches or by software settings) to apply filters to a camera by moving the polarizer(s) into place.

In the case that the device's camera is internally polarized, the polarized light source may be used in conjunction with camera's existing polarizer serving as the second polarizer. Or, the second polarizing filter can still be placed in front of the mobile device's camera to augment polarization the camera's existing polarization.

Combined Polarization

Polarizers can be applied in various combinations to both the camera and/or the light source, using individual filters on either or both, or multiple filters for use on either or both. The relative orientation of the polarization axes of the first polarizing filter of the illuminating source and the second polarizing filter of the camera may be altered to allow for cross (relative orientation 90 degrees), parallel (relative orientation 0 degrees), or variable polarized imaging (relative orientation any angle in between 0 and 90 degrees). For example, a single polarizing filter may be applied to both the camera and flash, such that the camera and light would be parallel polarized. Or, one of the camera or the flash may be polarized independent of the other. In such case, the polarizer in front of the camera or light source can be repositioned to alter its axis of polarization to achieve the desired type of polarized imaging.

In embodiments, both the first and second polarizers the light source and camera can be contained in one housing that may be coupled to the mobile device. In such cases the housing functions to hold the first polarizing filter in front of the light source and the second polarizing filter in front of the camera. Either of the polarizers may be fixed in position or allowed to reposition to allow for cross, parallel or variable polarized imaging. For example, the first filter (placed in front of the light source) may be allowed to rotate 0 to 90 degrees, and the second filter (placed in front of the camera) may be fixed at 0 degrees or vice versa. The axis of polarization may be manually manipulated, or a polarizer may be moved by a motorized device, which may be manually or automatically switched (e.g., controlled by physical switches or by software settings) to change orientation of the filters or apply filters to a camera by moving the polarizer(s) into place.

Control

In embodiments, the mobile device may execute software to obtain polarized imagery in a desired manner via control of one or more of the camera, the light source, or either or both of the polarized filters. The light source may be controlled via software on the mobile device. The signal between the mobile device and the embodiment may be transmitted with a cable connecting the light source to the mobile device, radio signal (Bluetooth, WiFi, etc.), remote device or optical sensor (IR or flash). For example, both the intensity and color output of multiple individual LEDs can be controlled via software on the mobile device, which generates control signals transmitted to the light source from the mobile device, for example via Bluetooth. The camera may be controlled by native or installed software on the mobile device, or via signal from the polarizing device or remote device. For example the light source, or a camera of a mobile device, may have a trigger to synchronize the flash of the light source and the shutter on the mobile device camera, such that a button pushed on the light source or the mobile device may transmit a signal to the other of the light source or mobile device, via Bluetooth for example, to acquire an image. The axis of polarization of either polarizer may be moved by a motorized device, which may be manually or automatically controlled (e.g., controlled by physical switches or by software settings).

Use Cases

The embodiments may be employed in a number of use cases. For example, in dermatology the apparatus may be used in conjunction with a dermatoscope for more complete evaluation of a subject's skin. The dermatoscope is able to provide polarized images of individual lesions. The embodiments may be used for surface and subsurface inspection of larger skin regions which the dermatoscope cannot provide, such as pigmentation patterns of the face. In particular, when the polarization axes of polarizers covering the camera and light source are perpendicular to one another (i.e. cross-polarized), the light reflected from the surface of the skin can be excluded from the view of the camera, providing an unobstructed view of subsurface structures. Similarly, the polarization axes may be changed to highlight structures on the surface in the same field of view. Such complementary imagery may be viewed to enhance information of the skin to a viewer examining the imagery, such as a dermatologist or other medical practitioner.

In another use case, a patient with a skin condition may reside in a remote area with no reasonably accessible skin specialists. The patient may visit a local health clinic staffed by a nurse practitioner, and the practitioner may establish a video conference with a remote dermatologist. The dermatologist may view the conference on a display of a personal computer, and the remote practitioner may be using a smart phone. The dermatologist can direct the practitioner to apply certain polarization and other filters to a camera, light source, or both, of the smart phone, and to perform certain manipulations of the filters, imaging software, and the like. The dermatologist may thereby obtain imagery of the patient's skin far superior to what is possible with prior art practices. Alternatively or in addition, virtual or image based imagery can be obtained, which can be taken, stored, and forwarded to the dermatologist. Based at least in part on the imagery, the dermatologist may provide diagnoses, recommendations, and medical care to the patient that are also superior to what is possible with prior art practices.

Polarization can be combined with other light modifiers including spectral filters. In an exemplary use case in dentistry, cross-polarization can be combined with auto-florescent imaging for identification of cancerous and pre-cancerous oral lesions. In these cases, a blue filter may be coupled with the first (illuminating) polarizer and a yellow filer may be coupled with the second (optical receiver) filter. Here, the polarized blue filter placed in front of the illuminating source creates blue light that excites fluorophores located in the mucosa, which emit yellow light. The yellow light can pass through the polarized yellow filter placed in front to the camera while the blue light is mostly block by the yellow filter. Therefore, normal mucosa appears yellow-green. Since the expression of fluorophores decreased in cancer cells, area of concern for pre-cancer and cancer appear dark. In this use case, cross-polarization may be used to further minimize the amount of glare caused by the blue light, which can obstruct visualization of the underlying fluoresced yellow light.

In another use case, embodiments may be used to image plants in a garden to inform the gardener with regard to the condition of the surfaces and subsurface structures of plants in the garden. Thereby, a more thorough assessment of the health of the garden may be obtained than is possible with prior art practices.

Other areas in which embodiments may be useful can include art photography, gemology, paleontology, forensics, or any area in which glare-free surface imagery and subsurface imagery of translucent and other material can be of use.

Housing

The housing may be a 3D structure holding the light source and the first polarizing filter positioned in front of the light source, with all other necessary components for the function of the device. The second polarizing filter may be contained in a separate housing or may be contained in the same housing as the light source and first polarizing filter.

Filters may be fitted or adhered to a housing, permanently or temporarily. The filters may be held in place or allowed to change position, allowing the axis of polarization to be altered. The housing may be repositioned to change the axis of polarization. The housing may be configured to move the filters into position in front of the camera and/or light source. The polarizer's axis of polarization may be manually manipulated, or the polarizer may be moved by a motorized device, which may be manually or automatically switched (e.g., controlled by physical switches or by software settings).

The housing may be coupled to the mobile device using adhesive, custom fitted parts, clips, or using other types of couplers. The housing may be permanently or temporarily attached to the mobile device. The housing may be coupled to a second housing, such as a phone case, which itself is coupled to the mobile device.

Post-Processing

Images acquired by the camera may be alternatively or additionally be processed by software to emphasize characteristics of interest. For example, the contrast, brightness, white balance, hue and/or saturation may be adjusted. Similarly, color channels may be modified, isolated or excluded (e.g. red channel in RGB color space) or the color space maybe changed (e.g. RGB color space to CKMY color space) for further enhancement of desired features. Algorithms may be used to process images.

FIGURES

FIGS. 1A through 1F illustrate aspects of an embodiment in which a polarizing filter is applied to a light source in a housing that may be coupled to a mobile device. FIG. 1A shows a light source with multiple LEDs connected to a circuit board. The LEDs may be powered by a rechargeable battery (not shown). The color of the LEDs may vary. The output color and intensity may be controlled manually, automatically, by optical sensor, or by software located on the light source or on a mobile device to which it is coupled. The LEDs may be controlled as a group or independently. The light emitted from the LEDs may be continuous or flash. The light source may contain a controller to trigger the camera shutter and other functions on the mobile device or may be controlled by the mobile device.

FIG. 1B shows the same light source in a housing that is coupled to the mobile device. A single polarizing filter has been placed in front of the LEDs of the light source. The polarizing filter may be coupled to the light source by an adhesive or fitted. The axis of polarization of the polarizer may be changed in a variety of ways. For example, the polarizer may be rotated, flipped, or exchanged. The housing may be rotated within the coupler, or the entire apparatus may be moved and coupled to the mobile device in a different orientation.

FIG. 1C shows an embodiment in which polarizing filters have individual housings for the various LED components. FIG. 1D is a plan view of a polarizing filter in which parallel lines represent the axis of polarization of the filter. The polarizing filter may be rotated, flipped, or exchanged in the housing to change the axis of polarization. FIG. 1E shows an illustrative embodiment of the housing having multiple polarizing filters, each filter for covering a different light source, such as the LEDs in the housing shown in FIG. 1A. The axis of polarization of the 4 quadrants shown may be the same or different. The housing with filters shown in FIG. 1E may be arranged so that select polarizing filters cover LEDs emitting select colors of light. For example, the horizontally polarized filters may cover LEDs that emit orange light, and the vertically polarized filters may cover LEDs that emit yellow light. FIG. 1F shows the housing of FIG. 1E flipped over. Flipping the housing causes the polarization axes to change such that the orange LEDs are now vertically polarized and the yellow LEDs are horizontally polarized.

Figure 2B:
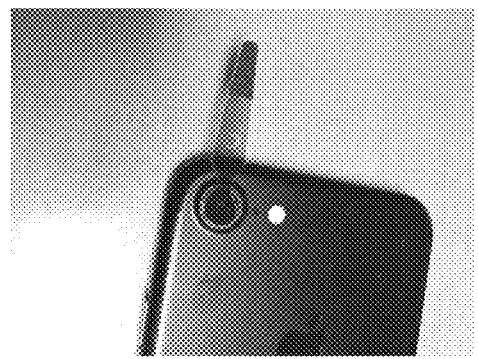
Figure 2C:
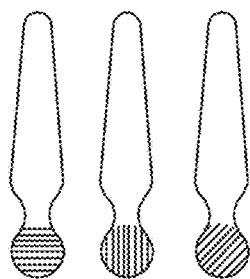
FIG. 2C shows polarizers with different polarization axes that may be applied to the camera of a mobile device.

FIGS. 2A and 2B show the coupling of another embodiment to a camera of an iPhone. As shown, the filter has a thin layer of optically clear adhesive on the surface that is directly applied to the camera lens. FIG. 2C is a drawing in which each filter has a plurality of parallel lines representing the axis of polarization of that filter, which can be selectively determined during manufacturing. These filters may be rotated, flipped, removed from the device and reapplied to its camera in a different orientation, or the filter may be exchanged for a different filter, for example, to change the axis of polarization.

Figure 3A:
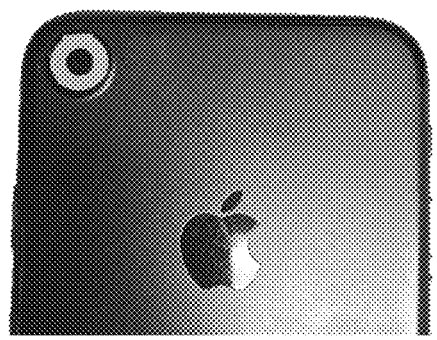
FIGS. 3A and 3B illustrate an embodiment comprising an annular ring of vinyl to which a filter is coupled, and the ring with filter is coupled to the mobile device's camera.
Figure 3B:
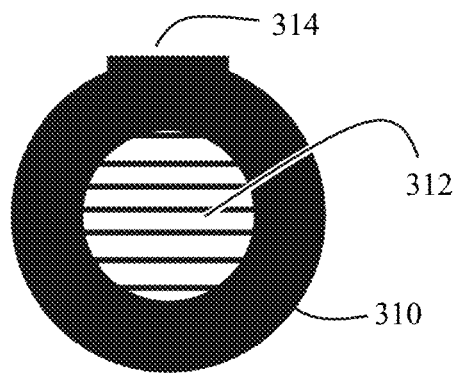

FIGS. 3A and 3B pertain to another exemplary embodiment, in which the second polarizer is coupled to the mobile device camera. As shown, this embodiment comprises a housing to which the filters are coupled. The housing is then coupled to the mobile device. FIG. 3A shows this embodiment applied to the camera of an Apple iPhone. FIG. 3B illustrates aspects of the embodiment in detail, comprising an annular ring 310 with an open central portion housing a polarizing filter element 312. The filter element 312 is coupled to one side of the ring, which has an identifying feature 314 indicating the direction of polarity of the filter. In embodiments, the ring may comprise vinyl material with adhesive on both sides, cut to match the circular perimeter of the filter. The filter is adhered to one side of the ring. To apply the filter to the mobile device, the adhesive on the other side of the ring may be pressed to the surface of the mobile device around its camera. Filter element 312 is also shown with horizontal lines representing the axis of polarization of the filter, which can be selectively determined during manufacturing.

Figure 4A:
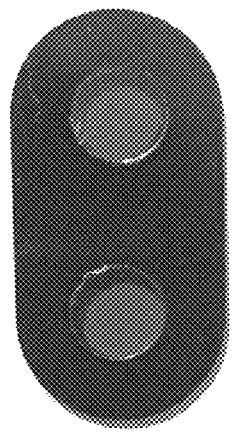
FIGS. 4A to 4D show aspects of an embodiment comprising a housing containing multiple polarizing filter elements having select axes of polarization, configured for use with cameras on a particular mobile device.
Figure 4B:
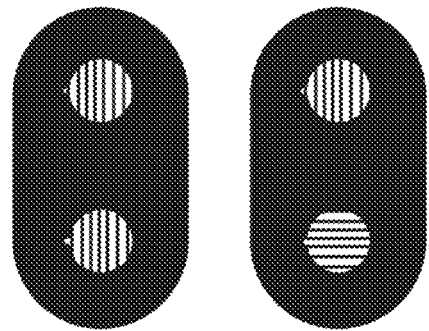
Figure 4C:
Figure 4D:
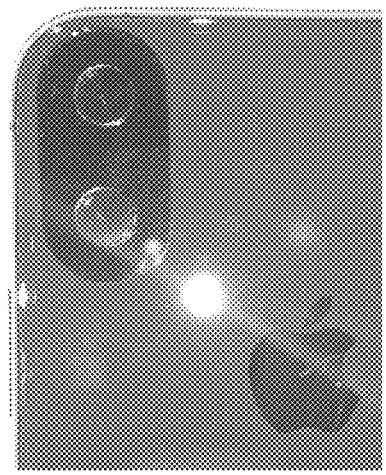

FIGS. 4A through 4D illustrate another exemplary embodiment in which a second polarizer is coupled to the mobile device camera. As shown in FIG. 4A, this embodiment comprises a housing that holds multiple filter elements. The filters may be fitted or adhered to the housing, and the housing with filters may be fitted or adhered to the mobile device. FIG. 4B shows two drawings of a housing coupled to two filters. The axes of polarization of the filters may point in the same direction, as shown in the housing on the left side of FIG. 4B. Alternatively, the axes of polarization of the filters may be orthogonal to each other, as shown in the housing on the right side of FIG. 4B. The housing in FIG. 4A is designed for use with the mobile device shown in FIG. 4C, which has multiple cameras. FIG. 4D shows the housing coupled to the mobile device of FIG. 4C. As shown, each filter element is held in place by the housing, positioned in the optical path of a corresponding camera lens.

Figure 5A:
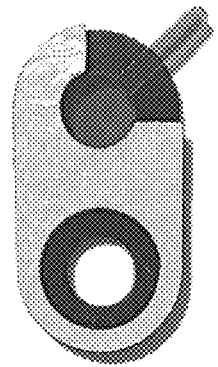
FIGS. 5A to 5E show aspects of filter housings having a polarized filter element that can be rotated to modify its axis of polarization in front of the camera of a mobile device to which it is coupled.
Figure 5B:
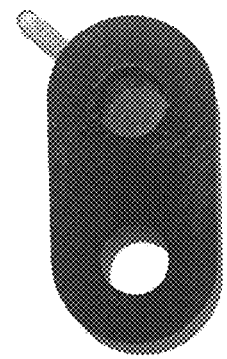
Figure 5C:
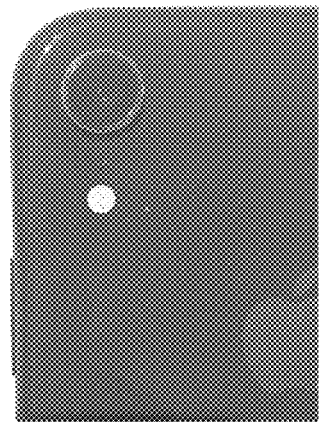
Figure 5D:
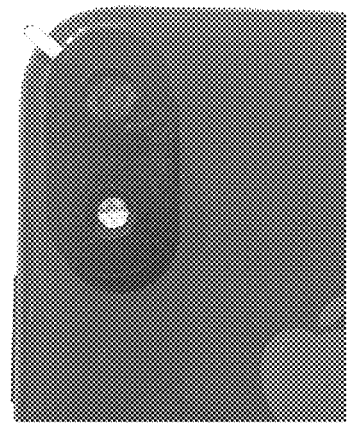
Figure 5E:
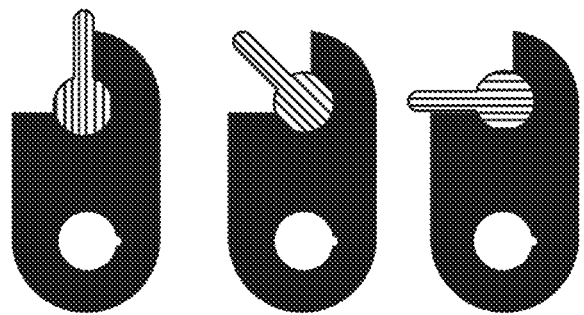

FIG. 5A shows the under surface of a housing designed for use with the particular mobile device shown in FIG. 5C. The housing has a rotating element in which the second polarizing filter is placed. The second polarizing filter has a lever extending from the periphery of a central circular portion which allows the filter to rotate between 0 and 90 degrees to change the axis of polarization. FIG. 5B shows the top surface of the housing. FIG. 5D shows the housing with filters coupled to the mobile device of FIG. 5C. The housing may be configured to be fitted or adhered to the mobile device, either temporarily or permanently. As shown, when the housing is coupled to the mobile device the rotating polarizing filter is positioned over a camera lens of the mobile device, and can be rotated between 0 and 90 degrees. FIG. 5E is a drawing of the housing with filter, with parallel lines indicating the axis of polarization of the rotating filter in three different positions as it rotates between 0 and 90 degrees.

FIGS. 6A through 6I pertain to another exemplary embodiment in which the housing contains a light source, a first polarizing filter positioned in front of the light source and a second polarizing filter to be positioned in front of the mobile device camera when the housing is coupled to the mobile device. FIG. 6A is a front view of a plurality of LEDs with circuitry and a battery, all of which are mounted in a housing that may be coupled to a mobile device. The LEDs are arranged in the shape of a ring and the housing contains an open area in the center, allowing for the device to be positioned around a mobile device camera. FIG. 6B shows a polarizer filter ring with a handle, designed to fit over the LEDs seen in FIG. 6A. In embodiments, the polarizer filter ring may be rotated, flipped or exchanged to alter the axis of polarization or modify other filter characteristics. FIG. 6C shows the second polarizing filter which may be placed in the housing to cover the open area of the device, which will be positioned over the mobile device camera. FIG. 6D shows a fully assembled embodiment 600 in which the first polarizer 610 is positioned in front of the LEDs, and the second polarizer 620 is arranged to cover the open area that will be positioned over the mobile device camera when the embodiment 600 is coupled to a mobile device. As shown, the first polarizer 610 has a lever positioned to the upper right, which can be rotated between 0 and 90 degrees to change its axis of polarization relative to the axis of polarization of the second polarizer 620.

FIG. 7A shows the apparatus 600 shown in FIG. 6D, now coupled to a mobile device. The apparatus is positioned on the mobile device so that the open area of the housing is disposed over the front-facing camera of the mobile device. In contrast, FIG. 7B shows the same apparatus coupled to the same mobile device, this time with the housing positioned on the mobile device so that its rear facing camera is disposed in the open area of the housing. FIG. 7C shows a side perspective view of the apparatus coupled to the mobile device. As shown, in this embodiment the apparatus has a spring-loaded clamp, although other types of couplers may be used.

FIGS. 7D and 7E show the polarization axes of the first and second filters, similar to those illustrated in FIG. 6D. As shown, in FIG. 7D the axes of polarization of the first filter 710 and second filter 720 are parallel. Either polarizing filter may be repositioned, for example rotated, flipped or exchanged to alter its axis of rotation. Although, this illustrative embodiment is configured so the first polarizer 710 may most conveniently be rotated. For example, FIG. 7E shows the first polarizer after it has been rotated 90 degrees from its position in FIG. 7D. Thus, in FIG. 7E the axes of polarization of the two filters are orthogonal.

Figure 8:
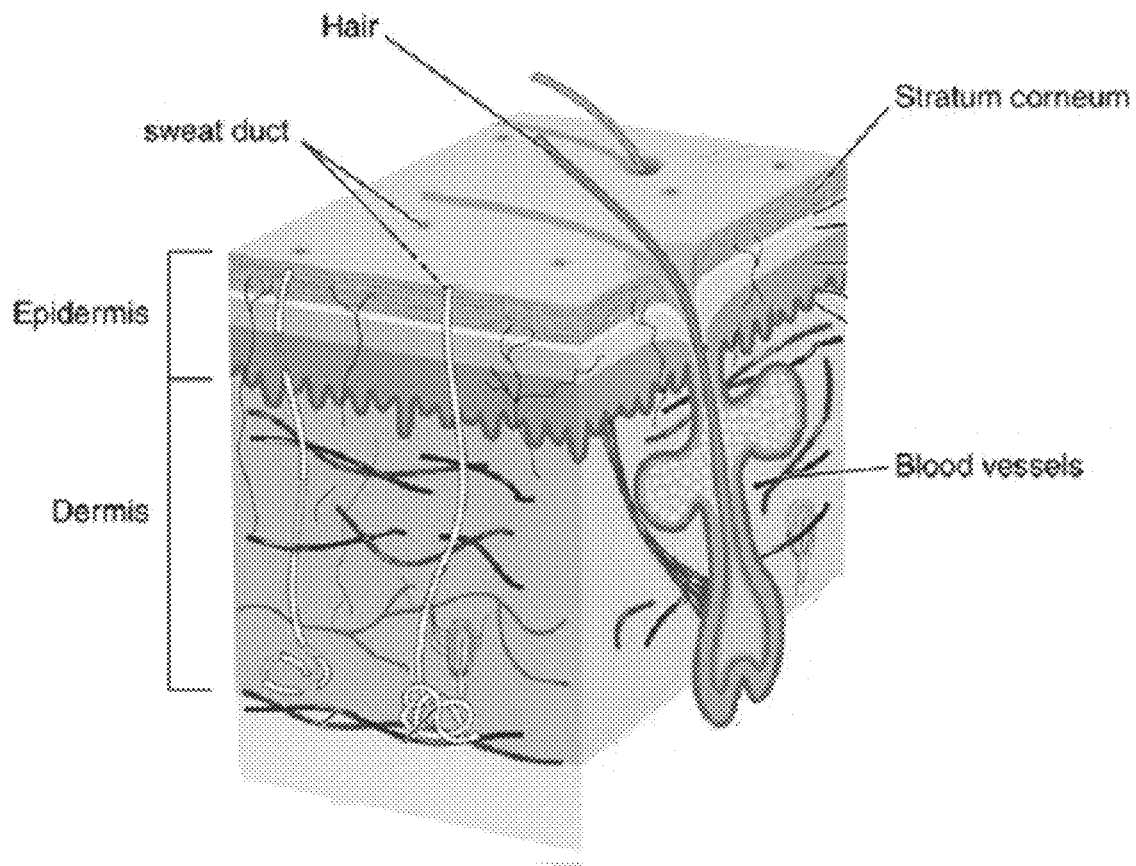
FIG. 8 is a perspective rendering of skin layers and structures therein.

FIG. 8 is a perspective view of a rendering of skin layers. The top layer of the skin is the stratum corneum, the top of which forms the skin outer surface. As previously disclosed, a pair of parallel polarized light source and camera filters provides for superior surface topography analysis, preferentially illuminating the skin surface while suppressing the background light transmitted through the deeper layers of skin. Conversely, a pair of orthogonally polarized light source and camera filters provides for superior subsurface analysis, preferentially illuminating the skin's subsurface structures while suppressing light reflected from the skin surface.

Figure 9A:
FIGS. 9A through 9I are views of a subject's face made possible by disclosed embodiments.
Figure 9B:
Figure 9C:
Figure 9D:
Figure 9E:
Figure 9F:
Figure 9G:
Figure 9H:
Figure 9I:
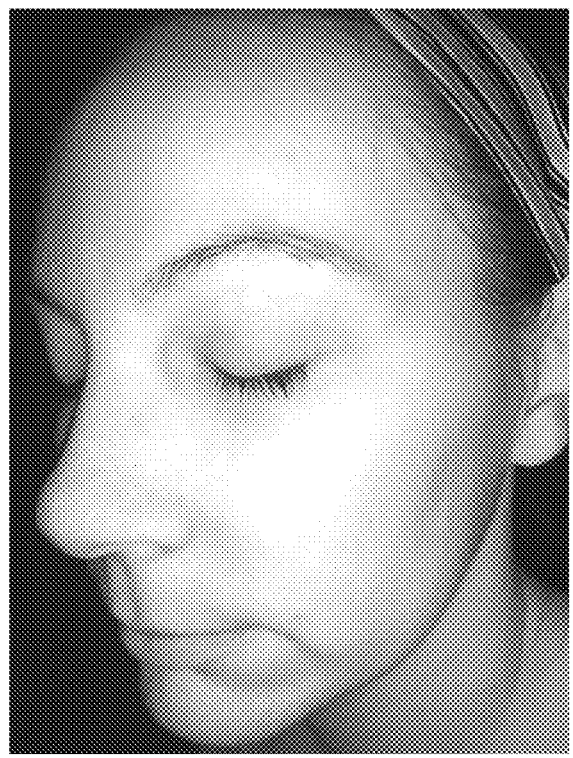

FIGS. 9A through 9I are illustrative of views of a subject's face made possible by disclosed embodiments. FIG. 9A is an unfiltered perspective view of the subject's face. This may be regarded as a baseline unenhanced image, while FIG. 9B is a magnified view of a portion of the view shown in FIG. 9A. FIG. 9C is an image taken using a light source covered by a first polarizing filter, and a camera lens covered by a second polarizing filter, wherein the filters' axes of polarization are oriented in parallel. FIG. 9D is a magnified view of the subject seen in FIG. 9C. Skin surface topography is clearly visible, emphasizing features such as pores and wrinkles, while largely suppressing subsurface features such as blood vessels and pigment. Conversely, FIGS. 9E and 9F are an image and closeup taken using a pair of polarized light source and camera filters oriented orthogonally. Here, skin subsurface structures are preferentially imaged, showing features such as blood vessels and pigment, while largely suppressing surface features. FIG. 9G shows the result of software enhancement to emphasize pigmentation. FIG. 9H shows the result of software enhancement to emphasize vascularity. Other types of filters and enhancements may additionally or alternatively be applied. For example, FIG. 9I is an image captured using a 650 nm long pass filter in conjunction with the orthogonally polarized filters.

Figure 10:
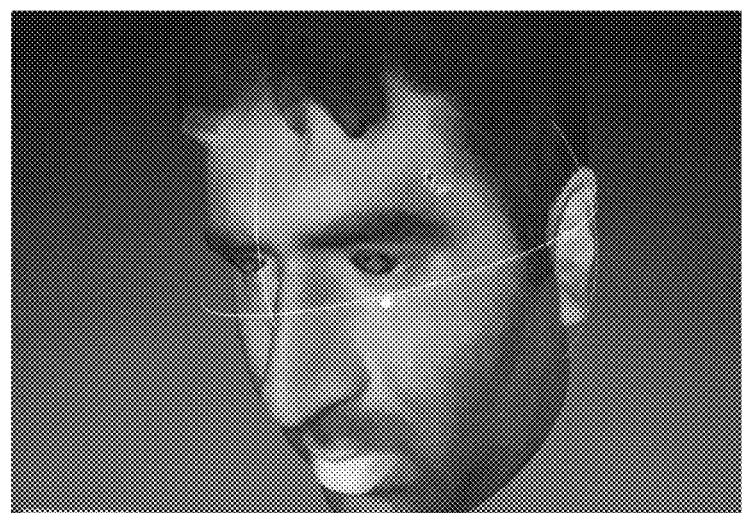
FIG. 10 is a representation of a 3 dimensional image generated by software using imagery obtained using the herein described apparatus.

FIG. 10 illustrates use of the invention in 3D imaging, in which a 2D photographic texture map of the face is acquired using cross-polarized imaging and processed with software, prior to being wrapped on a 3D model.

In summary, an apparatus is described for obtaining polarized imagery using a portable device. The apparatus comprises, a light source, a first polarizing filter configured to cover the light source, a second polarizing filter configured to cover the lens of a mobile device's built-in camera, one or more housing to contain the light source and filters, and couplers attached to the housings for coupling the housings to the mobile device. When the housing is coupled to the mobile device and the camera is operated, light from the light source passes through the first polarizing filter and passes as polarized light through an illuminating path to illuminate an object being imaged, and light from the illuminated object passes through an optical path and the second filter to the camera lens.

In embodiments, at least one of the filters is arranged to modify its polarization axis. The polarization axis may be modifiable to any angle between 0° and 90°. In embodiments, the first and second polarizing filters are linearly polarized. In other embodiments, at least one of the polarizing filters is not linearly polarized. For example, it may be circularly or elliptically polarized.

In embodiments, the apparatus further comprises a light modifying element disposed adjacent to at least one of the polarizing filters in a stacked configuration. The light modifying element may be one of a band pass filter, a short pass filter, a long pass filter, a narrow band filter, a Fresnel lens, a concave lens, a convex lens, an aspheric lens, a compound lens, a prism, a mirror, a contrast enhancing diffuser, a neutral density diffuser, a diffraction grating, an optical fiber, and a beam splitter.

In embodiments, the apparatus comprises a mechanism, either wireless or wired, for sending and receiving signals to the mobile device. In embodiments, a cable may couple the apparatus to the mobile device for passing signals between the apparatus and the mobile device. The cable may plug into a port of the mobile device, and may provide power from the mobile device to operate the apparatus. In embodiments, a radio signal between embodiment and mobile device may wirelessly transmit signals.

In aspects of embodiments, a computer readable storage device contains computer readable instructions which, when executed on a processor of a mobile device containing a built-in camera and a power source, cause the mobile device to trigger an operation of an external light source covered by a polarizing filter, and to store imagery captured by the mobile device's built-in camera of an object illuminated by light from the external light source passing through the polarizing filter. In embodiments, the instructions may further cause the imagery to be processed. The instructions may also cause the imagery to be transmitted to a remote device. The imagery may be transmitted, for example, during a video conference with the remote device, and presented for viewing on a display of the remote device.

In aspects of embodiments, a method for obtaining imagery using a portable device may comprise coupling to the mobile device a light source covered by a first polarizing filter, and a second polarizing filter arranged to cover a lens of a camera built into the mobile device. The light source is activated to emit light to illuminate an object being imaged, wherein light from the light source passes through the first polarizing filter to polarize the light, the polarized light passes through an illuminating path to illuminate the object, and light from the illuminated object passes through an optical path to the camera. The housing may be configured to modify the polarization axis of the polarizing filter in the illumination path. A light modifying element may be placed adjacent to at least one of the polarizing filters in a stacked configuration. The light modifying element may be one or more of a band pass filter, a short pass filter, a long pass filter, a narrow band filter, a Fresnel lens, a concave lens, a convex lens, an aspheric lens, a compound lens, a prism, a mirror, a contrast enhancing diffuser, a neutral density diffuser, a diffraction grating, an optical fiber, and a beam splitter.

Although the invention has been described and illustrated in exemplary forms with a certain degree of particularity, it is noted that the description and illustrations have been made by way of example only. Numerous changes in the details of construction, combination, and arrangement of parts and steps may be made without deviating from the scope of the invention. Accordingly, such changes are understood to be inherent in the disclosure. The invention is not limited except by the appended claims and the elements explicitly recited therein. The scope of the claims should be construed as broadly as the prior art will permit. It should also be noted that all elements of all of the claims may be combined with each other in any possible combination, even if the combinations have not been expressly claimed.

What is claimed is:

1. An apparatus for obtaining polarized imagery of a subject's skin, the apparatus comprising:
   a light source;
   a first polarizing filter;
   a second polarizing filter;
   one or more housings containing the light source, the first polarizing filter, and/or the second polarizing filter; and
   a coupler attached to the one or more housings for coupling the one or more housings to a mobile device separate from the apparatus;
   wherein:
      the first polarizing filter is positioned such that the first polarizing filter covers the light source,
      the second polarizing filter is positioned such that the second polarizing filter covers a lens of the mobile device's built-in camera when the one or more housings are coupled to the mobile device,
      the one or more housings, the first polarizing filter, and/or the second polarizing filter are arranged such that a polarization axis of the first polarizing filter and/or a polarization axis of the second polarizing filter can be modified, and
      when the one or more housings are coupled to the mobile device and the camera is operated, light from the light source passes through the first polarizing filter and passes as polarized light along an illuminating path to illuminate the subject's skin, and light from the subject's skin passes along an optical path and through the second polarizing filter to the lens such that a polarized image of a region of the subject's skin can be captured by the camera.

2. The apparatus of claim 1, wherein the coupler is an adhesive, a form-fitted attachment, or a clamp.

3. The apparatus of claim 2, wherein the clamp comprises a spring-loaded hinge.

4. The apparatus of claim 1, wherein the first and second polarizing filters are contained in the same housing of the one or more housings.

5. The apparatus of claim 1, wherein the first and second polarizing filters are contained in separate housings of the one or more housings.

6. The apparatus of claim 1, wherein the polarization axis of the first polarizing filter and/or the polarization axis of the second polarizing filter can be modified to any angle between 0° and 90° relative to the other polarizing filter.

7. The apparatus of claim 1, wherein the first polarizing filter and the second polarizing filter are linearly polarized.

8. The apparatus of claim 1, wherein the first polarizing filter and/or the second polarizing filter is/are not linearly polarized.

9. The apparatus of claim 1, further comprising a light modifying element disposed adjacent to the first polarizing filter and/or the second polarizing filter in a stacked configuration.

10. The apparatus of claim 9, wherein the light modifying element is a band pass filter, a short pass filter, a long pass filter, a narrow band filter, a Fresnel lens, a concave lens, a convex lens, an aspheric lens, a compound lens, a prism, a mirror, a contrast enhancing diffuser, a neutral density diffuser, a diffraction grating, an optical fiber, or a beam splitter.

11. The apparatus of claim 1, wherein the region of the subject's skin has a dimension greater than 5 cm, and wherein the polarized image of the region of the subject's skin is in focus.

12. The apparatus of claim 1, wherein the second polarizing filter has a surface area greater than a surface area of the lens.

13. The apparatus of claim 1, wherein the one or more housings and the first polarizing filter are arranged such that a polarization axis of the first polarizing filter can be manually modified and/or modified by a motorized device.

14. The apparatus of claim 1, wherein the one or more housings and the second polarizing filer are arranged such that a polarization axis of the second polarizing filter can be manually modified and/or modified by a motorized device.

15. The apparatus of claim 1, wherein the polarization axis of the first polarizing filter and/or the polarization axis of the second polarizing filter can be modified between 0° relative to the other polarizing filter and 90° relative to the other polarizing filter.

16. The apparatus of claim 15, wherein the polarization axis of the first polarizing filter and/or the polarization axis of the second polarizing filter can be modified to at least one angle between 0° and 90° relative to the other polarizing filter.

17. A method for obtaining polarized imagery of a region of a subject's skin using a portable device, the method comprising:
   coupling the portable device to a mobile device separate from the portable device,
      wherein the portable device includes (i) a first polarizing filter between a light source and the subject's skin, (ii) a second polarizing filter positioned to cover a lens of a camera built into the mobile device when the portable device is coupled to the mobile device, and (ii) one or more housings containing the light source, the first polarizing filter, and/or the second polarizing filter, and
      wherein the first polarizing filter, the second polarizing filter, and/or the one or more housings are arranged such that a polarization axis of the first polarizing filter and/or a polarization axis of the second filter can be modified;
   activating the light source to emit light to illuminate the subject's skin, wherein light from the light source passes through the first polarizing filter to polarize the light, and wherein the polarized light passes along an illuminating path to illuminate the subject's skin, and further wherein light from the subject's skin passes through the second polarizing filter along an optical path to the lens; and capturing a polarized image of the region of the subject's skin using the camera while the polarized image is in focus.

18. The method of claim 17, further comprising placing a light modifying element adjacent to the first polarizing filter and/or the second polarizing filter in a stacked configuration, wherein the light modifying element is a band pass filter, a short pass filter, a long pass filter, a narrow band filter, a Fresnel lens, a concave lens, a convex lens, an aspheric lens, a compound lens, a prism, a mirror, a contrast enhancing diffuser, a neutral density diffuser, a diffraction grating, an optical fiber, or a beam splitter.

19. The method of claim 17, wherein the region of the subject's skin has a dimension greater than 5 cm.

20. A method for obtaining polarized imagery of a region of a subject's skin using a portable device, the method comprising:
- coupling the portable device to a mobile device separate from the portable device,
  - wherein the portable device includes (i) a first polarizing filter between a light source and the subject's skin, (ii) a second polarizing filter positioned to cover a lens of a camera built into the mobile device when the portable device is coupled to the mobile device, and (ii) one or more housings containing the light source, the first polarizing filter, and/or the second polarizing filter, and
  - wherein the first polarizing filter, the second polarizing filter, and the one or more housings are arranged such that a polarization axis of the first polarizing filter and/or a polarization axis of the second filter can be modified;
- activating the light source to emit light to illuminate the subject's skin, wherein light from the light source passes through the first polarizing filter to polarize the light, and wherein the polarized light passes along an illuminating path to illuminate the subject's skin, and further wherein light from the subject's skin passes through the second polarizing filter along an optical path to the lens;
- modifying the polarization axis of the first polarizing filter to alter a polarization of the light that passes along the illuminating path and/or modifying the polarization axis of the second polarizing filter to alter the polarization of the polarized light that passes along the optical path to the lens; and
- capturing a polarized image of the region of the subject's skin using the camera while the polarized image is in focus.

* * * * *